US006537240B2

United States Patent
Cavicchioli et al.

(10) Patent No.: US 6,537,240 B2
(45) Date of Patent: Mar. 25, 2003

(54) METHOD FOR DETERMINING THE RECIRCULATION OF BLOOD IN A VASCULAR ACCESS AND A SYSTEM FOR IMPLEMENTING SAME

(75) Inventors: Giovanni Cavicchioli, Medolla (IT); Enrico Canini, Modena (IT); Massimo Fava, Mirandola (IT)

(73) Assignee: Hospal AG, Basel (CH)

( * ) Notice: Subject to any disclaimer, the term of this patent is extended or adjusted under 35 U.S.C. 154(b) by 0 days.

(21) Appl. No.: 09/091,349

(22) PCT Filed: Oct. 17, 1997

(86) PCT No.: PCT/IB97/01289

§ 371 (c)(1),
(2), (4) Date: May 3, 1999

(87) PCT Pub. No.: WO98/17334

PCT Pub. Date: Apr. 30, 1998

(65) Prior Publication Data

US 2002/0062098 A1 May 23, 2002

(30) Foreign Application Priority Data

Oct. 18, 1996 (IT) .......................... TO96A0855

(51) Int. Cl.⁷ .......................... A61M 37/00; G02F 1/44

(52) U.S. Cl. .................... 604/5.01; 604/6.06; 604/6.09; 210/646

(58) Field of Search .......................... 604/4.01, 5.01, 604/28–30, 6.09, 6.11, 6.06; 210/645–646, 650–652, 739, 744, 767, 96.1–2, 97, 102–3, 790, 138–40, 321.6, 696, 321.71–72; 422/44, 48; 73/53.01, 54.01–2, 54.43, 61.43, 64, 861, 195–6; 600/300–1, 309, 320, 322, 326, 328, 468, 465, 504–7

(56) References Cited

U.S. PATENT DOCUMENTS

| 4,469,593 A | | 9/1984 | Ishihara et al. ............ 210/96.2 |
| 5,098,373 A | | 3/1992 | Polaschegg |
| 5,312,550 A | | 5/1994 | Hester |
| 5,510,716 A | * | 4/1996 | Buffaloe, IV et al. .......... 604/4 |
| 5,510,717 A | * | 4/1996 | Buffaloe, IV et al. ...... 324/445 |
| 5,866,015 A | * | 2/1999 | Kramer |
| 6,075,367 A | * | 6/2000 | Brugger ..................... 324/439 |

FOREIGN PATENT DOCUMENTS

| EP | 0 547 210 | | 1/1996 |
| EP | 0 693 297 A1 | | 1/1996 |
| EP | 0693297 A | * | 1/1996 |
| WO | WO 96/08305 | | 3/1996 |

* cited by examiner

Primary Examiner—Angela D. Sykes
Assistant Examiner—Patricia Bianco
(74) Attorney, Agent, or Firm—Finnegan, Henderson, Farabow, Garrett & Dunner (57) ABSTRACT

In an extracorporeal blood treatment system, non-treated blood may be withdrawn from a patient through an arterial line connected to a first compartment of a blood treatment apparatus. The blood treatment apparatus also includes a second compartment separated from the first component by a semi-permeable membrane. Treated blood may be returned to the patient through a venous line connected to the second compartment. In order to determine blood recirculation, i.e., a mixture of treated blood and non-treated blood in the arterial line, the ultrafiltration rate of plasma water through the semi permeable membrane of the treatment apparatus may be temporarily increased or decreased, and the resulting variation of the blood concentration, i.e., of the ratio of the volume of the plasma volume to the blood volume, is determined. The extent of the mixture of the treated blood and the non-treated blood in the arterial line may then be calculated as a function of the blood flow rate in the treatment apparatus, of the amplitude of the variation of the ultrafiltration rate, and of at least two values of the blood concentration, determined before and during the variation of the ultrafiltration flow rate, respectively.

12 Claims, 5 Drawing Sheets

METHOD FOR DETERMINING THE RECIRCULATION OF BLOOD IN A VASCULAR ACCESS AND A SYSTEM FOR IMPLEMENTING SAME

BACKGROUND OF THE INVENTION

1. Field of the Invention

The present invention relates to a method for determining the blood recirculation in a vascular access.

The present invention applies in particular to determination of the blood recirculation in a vascular access during a dialysis treatment, which will be taken as a non-limiting example in the following description.

2. Description of Related Art

It is known that blood is composed of a liquid part, blood plasma, and of a corpuscular part formed by cells, including the red corpuscles which contain haemoglobin. In cases of renal insufficieny, undesirable substances of low moleular weight are also found in the blood, and these can be removed by a dialytic treatment carried out using a dialysis apparatus.

Dialysis treatments have an efficiency which is defined by the ratio between the volume of blood purified during the dialysis session, and the patient's total blood volume.

Figure 1:
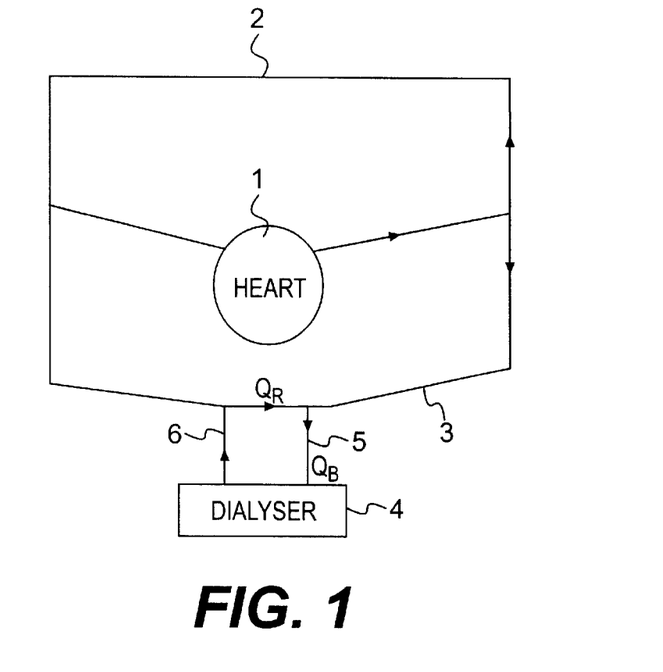
FIG. 1 represents a simplified model of the blood flows originating in the body of a patient connected to a circuit for the extracorporeal circulation of blood.

FIG. 1 illustrates a simplified model of the blood flows in a patient/extracorporeal circuit system, in which communication between the patient and the extracorporeal circuit takes place at a vascular access of the Cimino-Brescia fistula type. In this figure, the reference 1 denotes the heart, the reference 2 denotes the pulmonary circuit, the reference 3 denotes the vascular or systemic circuit, and the reference 4 denotes a dialyser which is connected to the systemic circuit 3 by means of a line 5 for withdrawing blood (arterial line) and a line 6 for returning blood (venous line).

As shown in FIG. 1, the blood which is treated during a dialysis session comes from the systemic circuit 3, in which the blood flows with a limited flow rate. For this reason, current dialytic treatments have a limited efficiency, and at the present time there are no corrective means allowing its value to be increased.

Figure 2:
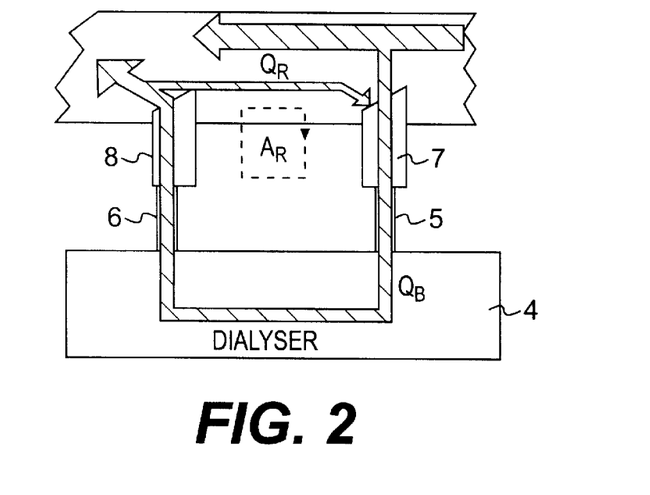
FIG. 2 is a simplified scheme of a vascular access and the blood flows circulating in it.

Furthermore, the efficiency of dialytic treatments is also reduced by the phenomenon which is known in the medical field by the term "recirculation in vascular access", the extent of which depends on multiple factors, such as the blood flow rate in the extracorporeal circuit, the position of the needles and the degree of stenosis of the fistula. The recirculation takes place when some of the blood which has been treated in the extracorporeal circuit is recirculated in this circuit via the arterial line 5 immediately after it has been injected into the vascular access 4 via the venous line 6. This phenomenon is illustrated in FIG. 2, where the references 7 and 8 denote the needles for withdrawing and returning the blood, respctively connected to the arterial line 5 and the venous line 6.

The value $A_R$ of the recirculation in the vascular access is defined by the following expression:

$$A_R\% = \frac{Q_R}{Q_B} 100 \tag{1}$$

in which QB is the blood flow rate circulating in the extracorporeal circuit, and QR is the blood flow rate returning into the extracorporeal circuit through the arterial line 5 immediately after the dialytic treatment.

Knowledge of the value AR of the recirculation in the vascular access presents several practical advantages in terms of dialysis treatments: it indicates that the needles 7, 8 should be repositioned when the value AR of the recirculation is too high, and it makes it possible to take action with a view to increasing the precision of the dialytic therapy, to monitor the stenosis of the fistula in the long term, and to increase the mean life of the fistula itself.

There are several known measurement methods for determining the value AR in the vascular access. These can be divided into two broad groups, the first comprising measurement methods which do not involve external action, and the second comprising those which do involve such action.

The first group includes measurement methods which do not involve chemical or physical action on the blood subjected to the dialysis treatment, and which do no more than quantify physiological parameters during the dialysis session.

One example from this group is the method consisting in measuring the urea concentration of three blood samples taken at the same time from the arterial line, the venous line and the patient's vascular circuit, and in calculating the value AR of the recirculation in the vascular access on the basis of the following equation (equivalent to equation 1):

$$A_R\% = \frac{C_S - C_A}{C_S - C_V} 100 \tag{2}$$

in which CS is the value of the urea concentration in the vascular circulation (systemic concentration), CA is the value of the urea concentration in the arterial line (arterial concentration), and CV is the value of the urea concentration in the venous line (venous concentration).

This method has the drawback of relying on the assumption that, when there is no recirculation in the vascular access, the value of the systemic concentration CS is equal to the value of the arterial concentration CA. However, it has recently been demonstrated that an assumption of this type is not valid under all conditions, and depends on the sampling point. There are therefore differences between these values, which compromise the reliability of the measurement, even when there is no recirculation in the vascular access.

The second group includes measurement methods which provide chemical or physical action on the blood subjected to a dialysis treatment.

An example from this second group is the measurement method which, like the previous one, consists in measuring the blood urea concentration in the arterial line, the venous line and the patient's vascular circuit. However, unlike in the method mentioned above, when the blood is being sampled from the arterial line in order to determine the value CS of the systemic concentration, the blood flow rate QB circulating in the extracorporeal circuit is set to a minimum in order to limit the recirculation in the fistula as far as possible, and therefore to reduce the differences between the values CS and CA of the systemic concentration and the arterial concentration.

Another example from the second group is the method consisting in imparting a tracer to the patient's blood in order to obtain chemical or physical dilution of the blood, and in simultaneously using specific sensor means to monitor the progress of the blood in the arterial line or in the venous line, or in both lines. Comparison between the integrals of the signals picked up by the sensors makes it possible to determine the value AR of the recirculation in the vascular access.

In particular, a first known method consists in measuring the temperature of the blood by means of temperature sensors which are arranged along the venous line and along the arterial line, so as to observe the relative temperature profile in response to a quantity of heat (here considered as a tracer) administered to or taken from the blood by means of the dialysis apparatus.

A second known measurement method, based on diluting the blood, is described in U.S. Pat. No. 5,312,550. According to this patent, provision is made for a substance having different physical properties from blood to be injected into the venous line, and for the blood recirculation in the vascular access to be detected by measuring the physical properties of this substance upstream of the point where the substance is injected.

A third known measurement method, based on diluting the blood, is described in U.S. Pat. No. 5,510,717. According to this patent, provision is made for a bolus of a hypertonic solution (tracer) to be injected into the venous line, and for the blood conductivity to be measured using two sensors which are arranged on the venous line and on the arterial line, in order to monitor the relative conductivity variation in response to injection of the bolus.

A fourth known measurement method, based on diluting the blood, consists in injecting a bolus of an isotonic solution (tracer) into the arterial line, upstream of a device for measuring optical absorption which is arranged on this line. The value AR of the recirculation in the vascular access is obtained by comparing the measurement taken by the optical device immediately after injection of the bolus with the measurement which is taken after the bolus has been partially recirculated in the extracorporeal circuit via the arterial access.

The object of the present invention is to produce a method for determining the value of the blood recirculation in an extracorporeal circuit, which is simple and entirely automatic, and which makes it possible to reduce the measurement errors and to use a small number of sensors, which in general already form part of a dialysis apparatus.

To achieve this object, the invention provides a method for determining the blood recirculation in a vascular access of a patient whose blood is subjected to treatment in a blood treatment apparatus, which is connected to the patient by an extracorporeal circuit comprising an arterial line, interconnecting the vascular access with an inlet of the treatment apparatus, and a venous line, interconnecting an outlet of the treatment apparatus with the vascular access, characterized in that it includes the steps of:

inducing a blood concentration in the treatment apparatus;

determining a parameter signifying the blood concentration in the arterial line, for example the blood haemoglobin concentration; and calculating the blood recirculation on the basis of the measured values of the parameter.

According to one embodiment of the invention, the method comprises the steps of:

setting the blood flow rate in the extracorporeal circuit to a determined value (QB);

determining a first value (HGBA0) of the parameter signifying the blood concentration in the extracorporeal circuit;

inducing a first variation, of determined amplitude (QUF), of the ultrafiltration rate in the treatment apparatus;

determining a second value (HGBA3) of the parameter signifying the blood concentration in the arterial line;

calculating the blood recirculation (AR) in the extracorporeal circuit as a function of the blood flow rate (QB), of the determined amplitude (QUF) of the first variation of the ultrafiltration rate, and of the first and second values (HGBA0, HGBA3) of the parameter signifying the blood concentration in the arterial line.

According to one characteristic of the invention, the step of determining a second value (HGBA3) of the parameter signifying the blood concentration in the arterial line comprises the steps of:

inducing a second variation of the ultrafiltration rate in the treatment apparatus, with the opposite amplitude to the amplitude of the first variation;

determining a third and a fourth value (HGBA1, HGBA2) of the parameter signifying the blood concentration in the arterial line, before the first variation of the ultrafiltration rate and after the second variation of the ultrafiltration rate, respectively;

determining an interpolation line between the third and fourth values (HGBA1, HGBA2) of the parameter signifying the blood concentration;

determining a steady-state value of the parameter signifying the blood concentration in the arterial line after the first variation of the ultrafiltration rate;

correcting the steady-state value of the parameter signifying the blood concentration in the arterial line, on the basis of the interpolation line, in order to obtain the second value (HGBA3) of the parameter signifying the blood concentration in the arterial line.

According to another characteristic of the invention, the treatment apparatus is a dialyser in which a dialysis liquid is circulated, and the circulation of the dialysis liquid is interrupted prior to the step of determining a first value (HGBA0) of the parameter signifying the blood concentration in the extracorporeal circuit.

The invention also relates to a blood treatment system comprising:

a blood treatment apparatus, an arterial line, intended to interconnect a vascular access of a patient with an inlet of the treatment apparatus, a venous line intended to interconnect an outlet of the treatment apparatus with the vascular access, means for inducing a blood concentration in the treatment apparatus;

means which are intended to determine a parameter signifying the blood concentration and are arranged on the arterial line;

characterized in that it includes computation and control means for:

driving the means for inducing a blood concentration, storing values of the parameter signifying the blood concentration, and calculating the blood recirculation on the basis of the values which the parameter takes in response to a determined drive program of the means for inducing a blood concentration.

BRIEF SUMMARY OF THE DRAWINGS

Other characteristics and advantages of the invention will become more apparent on reading the following description. Reference will be made to the apppended drawings, in which.

DESCRIPTION OF EXEMPLARY PREFERRED EMBODIMENTS

Figure 3A:
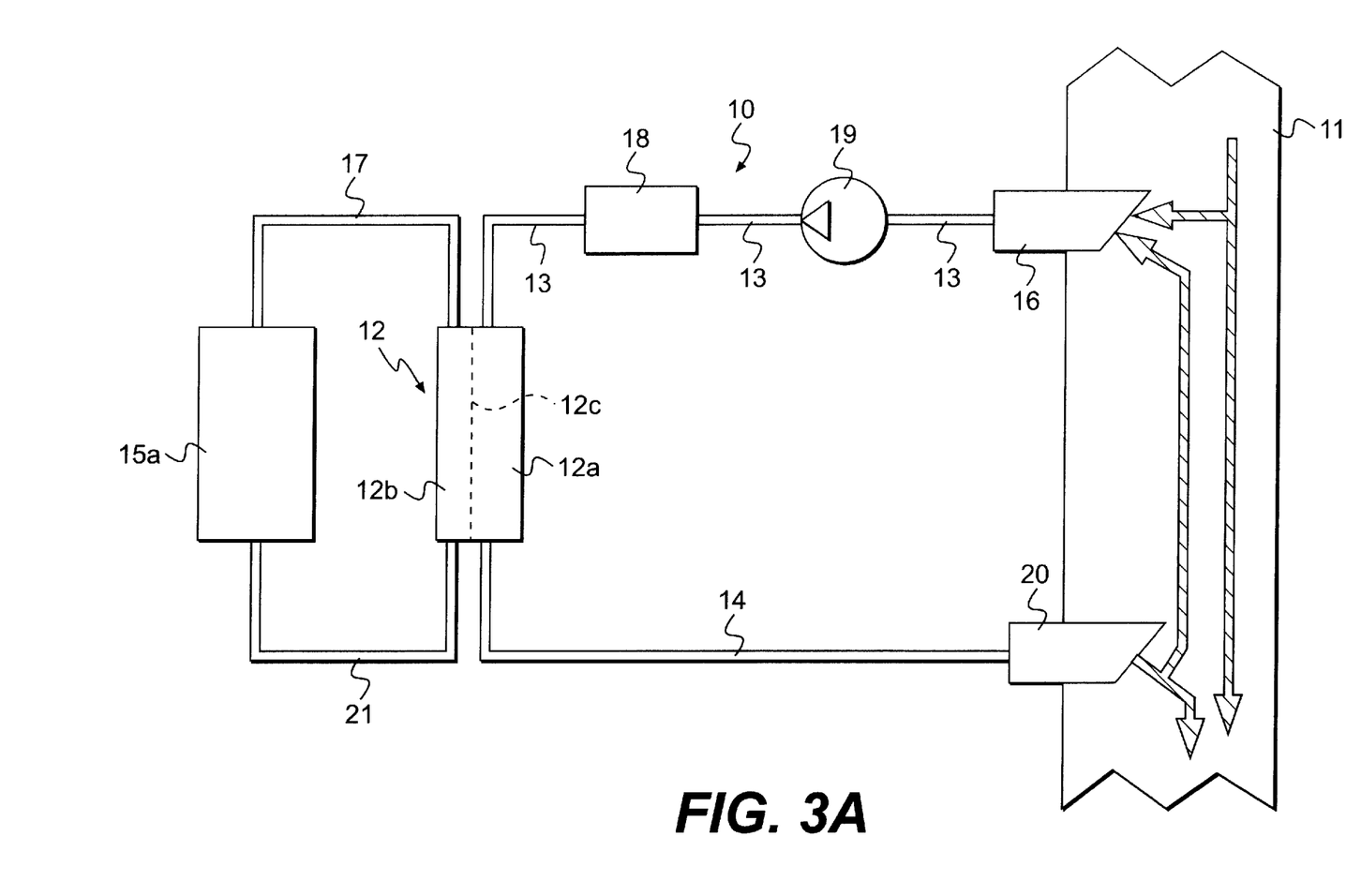
FIGS. 3A and 3B are simplified exemplary dialysis system schemes.
Figure 3B:
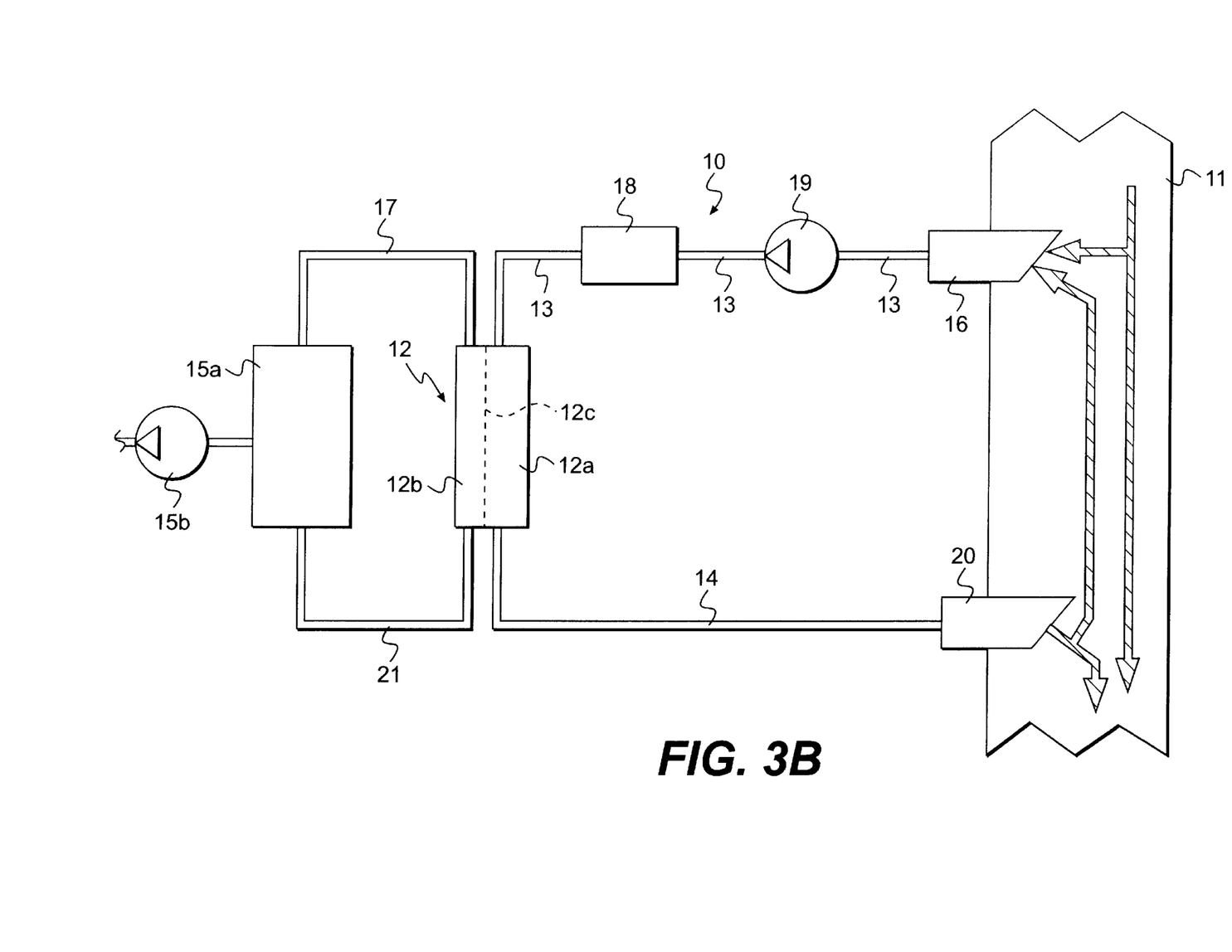

In FIGS. 3A & 3B, the reference 10 denotes an extracorporeal circuit for treating blood, which is connected to a fistula 11 (vascular access) of a patient who is being subjected to a dialysis treatment. FIGS. 3A & 3B represent only the elements of a dialysis system which are useful for understanding the method according to the invention.

The extracorporeal circuit 10 comprises a dialyser 12, having a blood compartment 12a and a compartment 12b for the dialysis liquid which are separated by a semipermeable membrane 12c. An arterial line 13 connects the patient's fistula 11 to an inlet of the blood compartment 12a, and a venous line 14 connects an outlet of the blood compartment 12a to the fistula 11. The arterial line 13 and the venous line 14 are connected to the fistula 11 by means of cannulas 16, 20, the arterial cannula 16 being fitted upstream of the venous cannula 20, relative to the direction in which the blood circulates in the fistula 11. In the direction in which the blood circulates, a blood pump 19 and a device 18 for measuring haemoglobin are arranged along the arterial line 13.

The compartment 12b of the dialysser 12 for the dialysis liquid has an inlet and an outlet which are connected to a dialysis machine 15a, respectively via a pipe 17 for supplying fresh dialysis liquid, and a pipe 21 for removing spend liquid. The dialysis machine 15a comprises, in particular, an ultrafiltration pump 15b allowing the passage of plasma fluid through the membrane 12c of the dialyser to be induced.

The dialysis system represented in FIGS. 3A & 3B also comprises a computation and control unit. This unit is connected to a user interface through which it receives instructions, for example various target values. It also receives information from the measuring components of the system, for example, the haemoglobin measurement device 18. On the basis of the instructions which it receives, and the operating modes and programmed algorithms, it drives the motor components of the system, for example, the blood pump 19 and the ultrafiltration pump 15b.

FIG. 3 furthermore shows the blood flows in the vascular access.

Figure 4:
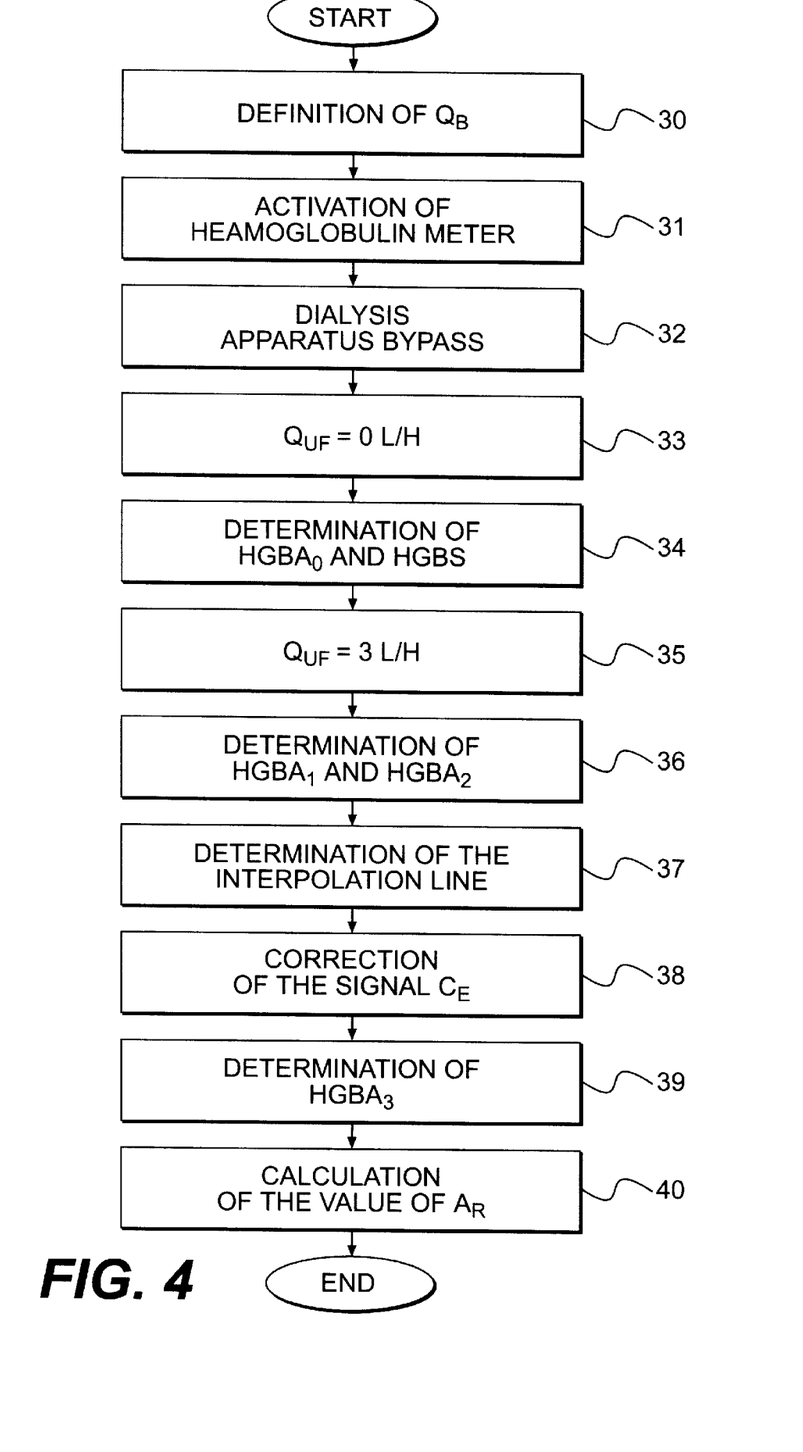
FIG. 4 is a flow chart of the operations carried out by the systems in FIGS. 3A and 3B in order to implement the method according to the invention.

When the dialysis system is functioning, the operations described below with reference to FIG. 4 are carried out.

The method for determining blood recirculation according to the invention is based on a variation in a blood characteristic induced by the ultrafiltration pump, namely the blood concentration.

At the start of the dialysis session, as shown in FIG. 4, the delivery rate of the blood pump 19 is set to a value QB (step 30).

The haemoglobin meter 18 is then turned on to acquire and store the concentration signal CE throughout the measurement needed for determining the recirculation (step 31).

The circulation of the dialysis liquid in the dialyser 12 is then interrupted (step 32) so that, after an initial transient period, the dialysis liquid in the dialyser has the same electrolytic concentration as the blood. The circulation of the dialysis liquid in the dialyser 12 is reestablished only when the measurements needed for determining the recirculation have been taken.

This operation makes it possible to limit the undesirable influence of possible osmotic imbalances on the haemoglobin concentration, because of which imbalances, even when no ultrafiltration has taken place, there is generally a variation in the blood haemoglobin concentration value due to the displacement of the water contained in the blood cells and in the interstitial spaces.

The ultrafiltration pump 15b is then set so that the value QUF of the ultrafiltration rate in the dialyser 12 is substantially zero (step 33); the result of this is that the values HGBA and HGBV of the haemoglobin concentrations in the arterial line 13 and in the venous line 14 are equal.

Next, on the basis of the concentration signal CE, the instantaneous value HGBA0 of the haemoglobin concentration in the arterial line 13 is determined, this being equal to the value HGBS of the systemic haemoglobin concentration when the ultrafiltration rate is zero (step 34). The relationship HGBS=HGBA0 is thus set.

The ultrafiltration pump 15b is then set so that the ultrafiltration rate QUF is equal to a determined value for a determined time interval. For example an ultrafiltration rate QUF equal to 3 l/h is set for 5 minutes (step 35); the variation in the ultrafiltration rate QUF as a function of time is represented for this example in the diagram of FIG. 5.

Figure 5:
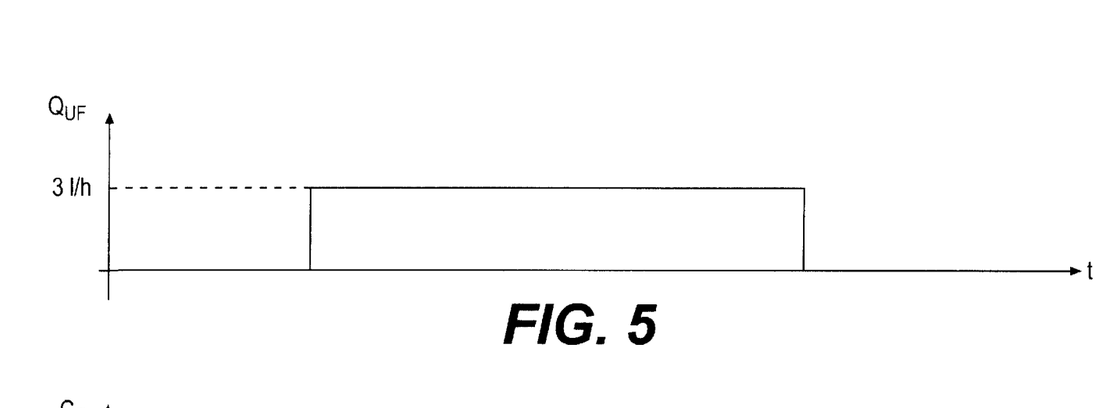
FIGS. 5, 6 and 7 are diagrams representing the variation as a function of time in the parameters measured or monitored during the implementation of the method according to the invention.

The first change in the ultrafiltration rate QUF, from zero to the determined value, results in an increase of the value of the haemoglobin concentration of the blood reintroduced into the patient's fistula 11 through the venous line 14, while the second change in the ultrafiltration rate QUF, from the determined value to zero, causes a decrease in the haemoglobin concentration to a value close to the initial haemoglobin value.

On the basis of the concentration signal CE provided by the haemoglobin meter 18, it is possible to deduce the recirculation value in the fistula 11.

If there is no recirculation in the vascular access, the blood which is concentrated in the dialyser 12 during the ultrafiltration episode and is injected into the patient's body through the venous line 14 will travel a long way inside the patient's body before circulating in the dialyser 12 again.

Figure 6:
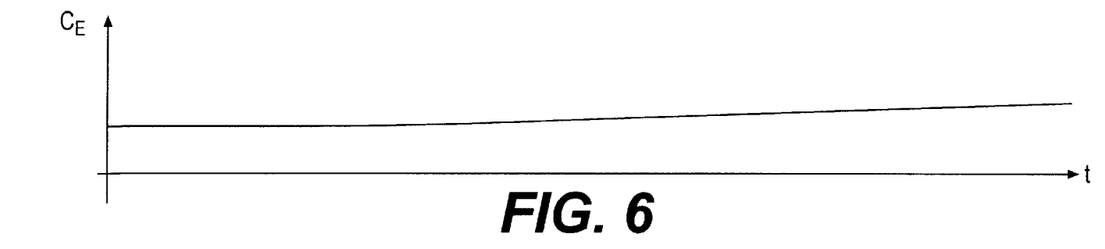

During this journey, the concentrated blood is subjected to such a dilution that the concentration signal CE produced by the haemoglobin meter 18 does not initially reveal any increase of the haemoglobin concentration in the arterial line 13 (as shown by the diagram in FIG. 6), and it will increase slightly only some minutes after the start of the ultrafiltration rate plateau (this is not shown in FIG. 6 because it is outside the time interval represented).

Figure 7:
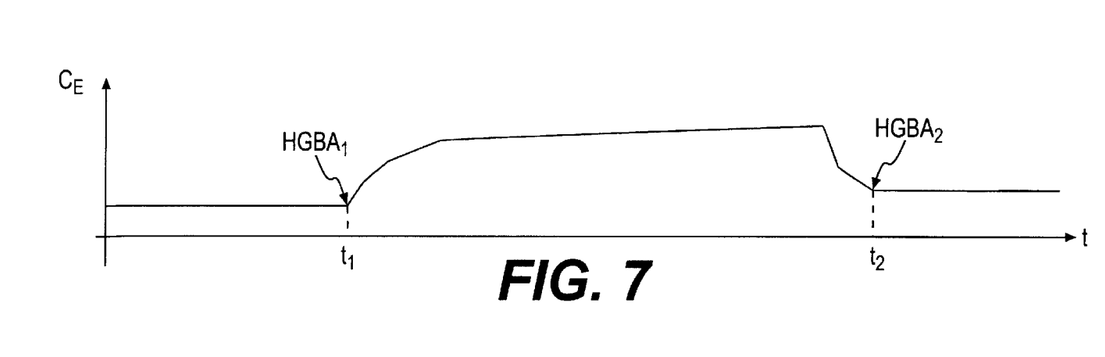

If, however, there is recirculation in the vascular access 11, some of the concentrated blood injected into the patient's body is immediately reintroduced into the arterial line 13, and the concentration signal CE provided by the haemoglobin meter 18 increases rapidly, as shown by the diagram in FIG. 7. In the example in question, this increase can be observed about one minute after the creation of an ultrafiltration regime, and reaches a substantially constant value after about three minutes.

The value AR of the recirculation in the fistula 11 is calculated on the basis of the value of the concentration signal CE which is taken in a steady state (steps 36 to 40).

The value AR of the recirculation in the fistula 11 is calculated while taking account of the "plasma refilling" phenomenon, according to which, when the plasma fluid is removed from the blood by ultrafiltration, the patient's body subjected to this treatment reacts and supplies the blood with water taken from the cells of the blood itself and from the interstitial spaces.

Specifically, the concentration signal CE, which the haemoglobin meter 18 produces in response to the first variation in the ultrafiltration rate, comprises a main component corresponding to the amplitude of the haemofiltration which is imposed, and a component, generally increasing linearly with time, corresponding to the difference between the ultrafiltration rate and the plasma refilling rate.

In order to eliminate this component, on the basis of the value of the stored concentration signal CE, the values HGBA1 and HGBA2 are determined, these being the values which the haemoglobin concentration in the arterial line 13 takes at the times, denoted t1 and t2 in FIG. 7, when it begins to increase at the start of the ultrafiltration episode and finishes decreasing at the end of the ultrafiltration episode, respectively (step 36).

When the plasma refilling rate is equal to the ultrafiltration rate, the values HGBA1 and HGBA2 are equal. However, the values HGBA1 and HGBA2 differ when the refilling rate is zero or is less than the ultrafiltration rate, HGBA2 being greater than HGBA1.

The equation of the interpolation line passing through the points HGBA1 and HGBA2 in FIG. 7 is then determined, which represents the variation in the undesirable component of the concentration signal CE as a function of time, this component generally being one which increases linearly as a function of time (step 37).

The concentration signal CE is then corrected for the effect of the plasma refilling phenomenon by subtracting the interpolation line from the concentration signal CE which the haemoglobin meter 18 produces during the haemofiltration episode, and is stored in the control and computation unit (step 38).

The value HGBA3 of the haemoglobin concentration in the arterial line 13 is then determined on the basis of the value taken in steady state by the corrected concentration CE. For example, this value may be the value measured at a determined time (for example 3 minutes) after the start of the ultrafiltration episode (step 39).

The value HGBA3 of the haemoglobin concentration in the arterial line 13 may also be calculated in the following way: on the basis of a series of values of the blood concentration, which are sampled starting from t1, the computation unit determines the equation of the curve representing the variation in the blood concentration, then calculates its asymptote. The haemoglobin concentration HGBA3 is chosen to be equal to this asymptote. The benefit of this way of determining HGBA3 is that it allows the duration of the haemofiltration episode to be reduced substantially.

Finally, the value AR of the recirculation in the fistula 11 is calculated using the following equation (step 40):

$$A_R\% = \frac{Q_B - Q_{UF}}{Q_B + Q_{UF}\left(\frac{HGBS}{HGBA_3 \pm HGBS}\right)} 100$$

in which QB is the delivery rate of the blood pump 19 (set in step 30), QUF is the ultrafiltration rate (set in step 35), HGBS is the systemic concentration (calculated in step 34) and HGBA3 is the arterial concentration (calculated in step 39).

The advantages of the present measurement method are as follows.

Above all, the present method is simple to use, in contrast to methods which do not involve external action, and which require blood samples and laboratory examinations, and also in contrast to methods which involve external action, and require manual intervention (injection of saline solution).

Furthermore, the present method can be implemented fully automated.

Furthermore, the method uses only one sensor, the haemoglobin meter 18, instead of two like many of the methods described above, and it therefore makes it possible to reduce the measurement errors.

Lastly, the method does not require any modification to the dialysis apparatus 10, since modern dialsis systems generally include a haemoglobin meter 18 and an ultrafiltration pump 15b.

Finally, it is readily apparent that the method described and illustrated here may have modifications and variants made to it without thereby departing from the scope of the present invention.

For example, in one variant of the method, the initial ultrafiltration rate has a non-zero determined value, and the variation of the ultrafiltration rate which is induced in order to measure the blood recirculation in the vascular access may be positive or negative (increase or decrease in the ultrafiltration rate by a determined amount).

In this case, the method provides for:

measuring the instantaneous value HGBA0 of the haemoglobin concentration in the arterial line 13 when the ultrafiltration rate is equal to its initial determined value, setting the ultrafiltration rate to a negative plateau, determining the value HGBA3 of the haemoglobin concentration in the arterial line 13, equalizing the value HGBS of the systemic haemoglobin concentration with the value HGBA3 when the ultrafiltration rate takes a zero value during this step (HGBS=HGBA3), correcting this value on the basis of the interpolation line in the manner described above, and calculating the value AR of the recirculation in the vascular access using the following equation:

$$A_R\% = \frac{Q_B - Q_{UF}}{Q_B + Q_{UF}\left(\frac{HGBS}{HGBA_0 \pm HGBS}\right)} 100$$

The present method may furthermore be employed, with comparable precision, when, because of a variety of factors such as movements and hydric and osmotic imbalances, the plasma refilling phenomenon adds more water to the blood than the quantity of plasma fluid removed by ultrafiltration, that is to say decreases the haemoglobin concentration in the blood. In this case, the undesirable component of the concentration signal produced by the haemoglobin meter 18 has a profile which decreases linearly with time.

What is claimed is:

1. Method for determining a mixture of treated blood and non-treated blood in an arterial line connecting a vascular system of a patient to an inlet of a first compartment of a blood treatment apparatus having first and second compartments separated by a semi-permeable membrane, the treated blood flowing in a venous line connecting an outlet of the first compartment to the patient's vascular system, the method comprising:

circulating blood, at a determined blood flow rate (QB), in an extracorporeal blood circuit including the arterial line, the first compartment, and the venous line;

determining, in the extracorporeal blood circuit, a first value (HGBAO) of a blood parameter indicative of a ratio of blood plasma volume to blood volume;

inducing a first variation in the value of the blood parameter by varying an ultrafiltration rate of plasma water through the semi-permeable membrane by a determined amplitude (QUF);

determining a second value (HGBA3) of the blood parameter in the arterial line; and calculating an extent ($A_R$) of the mixture of the treated blood and the non-treated blood in the arterial line as a function of the blood flow rate (QB), the amplitude (QUF) of the variation of the ultrafiltration rate, and of the first and second values (HGBAO, HGBA3) of the blood parameter.

2. Method according to claim 1, wherein determining a second value (HGBA3) of the blood parameter comprises:

determining a third value (HGBA1) of the blood parameter in the arterial line before inducing the first variation of the value of the blood parameter;

inducing a second variation, having an amplitude opposite to the amplitude of the first variation, in the value of the blood parameter by varying the ultrafiltration rate of plasma water through the semi-permeable membrane of the treatment apparatus;

determining a steady-state value of the blood parameter in the arterial line after inducing the first variation in the value of the blood parameter and before inducing the second variation in the value of the blood parameter;

determining a fourth value (HGBA2) of the blood parameter in the arterial line after inducing the second variation in the value of the blood parameter;

determining an interpolation line between the third and fourth values (HGBA1, HGBA2) of the blood parameter; and calculating the second value (HGBA3) of the blood parameter in the arterial line from the steady-state value of the blood parameter and the interpolation line.

3. Method according to claim 2, wherein:

the third value (HGBA1) of the blood parameter in the arterial line is determined when the ratio of plasma volume to blood volume begins to vary in response to the first variation of the ultrafiltration rate, and the fourth value (HGBA2) of the blood parameter in the arterial line is determined when the ratio of plasma volume to blood volume stops varying in response to the second variation of the ultrafiltration rate.

4. Method according to claim 1, wherein the second value (HGBA3) of the blood parameter in the arterial line is determined after a determined period of time has lapsed following an inception of the first variation of the ultrafiltration rate.

5. Method according to claim 1, further including setting substantially equal to zero, the ultrafiltration rate of plasma water through the semi-permeable membrane of the treatment apparatus before inducing the first variation in the ultrafiltration rate.

6. Method according to claim 1, wherein the first variation in the value of the blood parmeter is caused by increasing the ultrafiltration rate of plasma water through the semi-permeable membrane of the treatment apparatus.

7. Method according to claim 1, wherein the extent ($A_R$) of the mixture of the treated blood and the non-treated blood in the arterial line is calculated using the following equation:

$$A_R\% = \frac{Q_B - Q_{UF}}{Q_B + Q_{UF}\left(\frac{HGBS}{HGBA_3 \pm HGBS}\right)} 100$$

where:

QB is the blood flow rate in the extracorporeal circuit;

QUF is a predetermined amplitude of a first variation of the ultrafiltration rate;

HGBS is equal to the value (HGBA 0) of the blood parameter in the extracorporeal blood circuit before inducing the first variation of the ultrafiltration rate; and HGBA 3 is the second value of the blood parameter in the arterial line.

8. Method according to claim 1, wherein inducing a first variation in the ultrafiltration rate comprises reducing an existing ultrafiltration rate until it becomes substantially equal to zero.

9. Method according to claim 8, wherein the extent ($A_R$) of the mixture of the treated blood and the non-treated blood in the arterial line is calculated using the following equation:

$$A_R\% = \frac{Q_B - Q_{UF}}{Q_B + Q_{UF}\left(\frac{HGBS}{HGBA_0 \pm HGBS}\right)} 100$$

where:

QB is the blood flow rate in the extracorporeal circuit;

QUF is a predetermined amplitude of the first variation of the ultrafiltration rate;

HGBA0 is the first value of the blood parameter in the extracorporeal blood circuit before inducing the first variation of the ultrafiltratration rate;

HGBS is a value of a systemic blood concentration, which equal to the second value (HGBA3) of the blood parameter in the arterial line.

10. Method according to claim 1, wherein the treatment apparatus is a dialyzer in which a dialysis liquid is circulated, and the circulation of the dialysis liquid is interrupted prior to the step of determining the first value (HGBA0) of the blood parameter in the extracorporeal circuit.

11. Method according to claim 1, wherein the blood parameter is haemoglobin concentration.

12. Blood treatment system comprising:

a blood treatment apparatus having a first compartment and a second compartment separated by a semi-permeable membrane;

an arterial line for connecting a patient's artereo-venous system to an inlet of the first compartment, and for withdrawing non-treated blood from the patient;

a venous line for connecting an outlet of the first compartment to the patient's artereo-venous system and for returning treated blood to the patient;

at least one pump for circulating blood in an extracorporeal blood circuit including the arterial line, the first compartment, and the venous line;

at least one ultrafilter for causing ultrafiltration of plasma water through the semipermeable membrane of the treatment apparatus;

means for determining, in the arterial line, a value of a blood parameter indicative of a ratio of plasma volume to blood volume;

a controller for controlling the at least one ultrafilter to vary an ultrafiltration rate of plasma water through the semi-permeable membrane by a determined amplitude (QUF) so as to induce a temporary variation in the value of the blood parameter;

a memory for storing at least a first value (HGBA0) of the blood parameter before inducing the blood parameter variation and for storing a second value (HGBA3) of the blood parameter during the variation of the blood parameter; and a processor for calculating an extent ($A_R$) of a mixture of the treated blood and the non-treated blood in the arterial line as a function of a blood flow rate (QB), the amplitude (QUF) of the variation of the ultrafiltration rate, and the first and second values (HGBA0, HGBA3) of the blood parameter.

* * * * *

UNITED STATES PATENT AND TRADEMARK OFFICE
CERTIFICATE OF CORRECTION

PATENT NO. : 6,537,240 B2
DATED : March 25, 2003
INVENTOR(S) : Cavicchioli et al.

It is certified that error appears in the above-identified patent and that said Letters Patent is hereby corrected as shown below:

Column 9,
Line 67, "parmeter" should read -- parameter --.

Column 10,
Lines 7-9, $"A_R\% = \dfrac{Q_B - Q_{UF}}{Q_B + Q_{UF}\left(\dfrac{HGBS}{HGBA_3 \pm HGBS}\right)} 100"$ should read -- $A_R\% = \dfrac{Q_B - Q_{UF}}{Q_B + Q_{UF}\left(\dfrac{HGBS}{HGBA_3 - HGBS}\right)} 100$ --.

Line 15, "(HGBA 0)" should read -- (HGBA0) --.
Line 18, "HGBA 3" should read -- HGBA3 --.
Lines 29-31, $"A_R\% = \dfrac{Q_B - Q_{UF}}{Q_B + Q_{UF}\left(\dfrac{HGBS}{HGBA_0 \pm HGBS}\right)} 100"$ should read -- $A_R\% = \dfrac{Q_B - Q_{UF}}{Q_B + Q_{UF}\left(\dfrac{HGBS}{HGBA_0 - HGBS}\right)} 100$ --.

Line 39, "ultrafiltratration" should read -- ultrafiltration --.
Lines 40-41, "which equal" should read -- which is equal --.
Line 52, "system comprising" should read -- system, comprising --.
Line 66, "semipermeable" should read -- semi-permeable --.

Signed and Sealed this

Nineteenth Day of August, 2003

JAMES E. ROGAN
*Director of the United States Patent and Trademark Office*